(12) United States Patent
Yamamoto

(10) Patent No.: US 8,696,343 B2
(45) Date of Patent: Apr. 15, 2014

(54) FOLDING APPARATUS

(75) Inventor: Hiroki Yamamoto, Kagawa (JP)

(73) Assignee: Unicharm Corporation, Shikokuchuo-Shi, Ehime-Ken (JP)

( * ) Notice: Subject to any disclaimer, the term of this patent is extended or adjusted under 35 U.S.C. 154(b) by 0 days.

(21) Appl. No.: 13/392,592

(22) PCT Filed: Aug. 31, 2010

(86) PCT No.: PCT/JP2010/064814
§ 371 (c)(1),
(2), (4) Date: May 1, 2012

(87) PCT Pub. No.: WO2011/025034
PCT Pub. Date: Mar. 3, 2011

(65) Prior Publication Data
US 2012/0207871 A1    Aug. 16, 2012

(30) Foreign Application Priority Data

Aug. 31, 2009   (JP) ................. 2009-200524

(51) Int. Cl.
*B29C 53/06*   (2006.01)
*B65H 45/22*   (2006.01)
(52) U.S. Cl.
USPC ........ 425/335; 425/364 R; 425/373; 493/439; 493/443
(58) Field of Classification Search
USPC .............. 425/335, 364 R, 373; 493/439, 440, 493/442, 443, 446, 447
See application file for complete search history.

(56) References Cited

U.S. PATENT DOCUMENTS

| 4,421,501 | A | 12/1983 | Scheffer |
| 5,137,505 | A | 8/1992 | Ishii |
| 6,432,235 | B1 | 8/2002 | Bleckmann et al. |
| 6,557,466 | B2 * | 5/2003 | Codde et al. ................. 493/442 |
| 6,780,265 | B2 | 8/2004 | Bleckmann et al. |
| 2004/0026919 | A1 | 2/2004 | Bleckmann et al. |
| 2004/0108043 | A1 | 6/2004 | Otsubo |
| 2004/0182491 | A1 | 9/2004 | Bleckmann et al. |

FOREIGN PATENT DOCUMENTS

| EP | 0067329 A2 | 12/1982 |
| JP | 61093225 U | 6/1986 |
| JP | 4021435 A | 1/1992 |
| JP | 4075966 A | 3/1992 |

(Continued)

OTHER PUBLICATIONS

International Search Report and Written Opinion for PCT/JP2010/064814 dated Nov. 30, 2010.

(Continued)

*Primary Examiner* — James Mackey
(74) *Attorney, Agent, or Firm* — Lowe Hauptman & Ham, LLP

(57) ABSTRACT

A sailor roll includes pressing rolls and a center roll provided between the pressing rolls the center roll configured to press a central region of a web. The portions of the web pressed down by the pressing rolls serve as a fold origin from which the web is folded. Each of the pressing rolls has a tapered shape in which the diameter becomes smaller toward the outer side in the cross direction CD. In other word, the pressing rolls respectively have tapered surfaces tapered toward a side region of the web.

5 Claims, 4 Drawing Sheets

(56) References Cited

FOREIGN PATENT DOCUMENTS

| | | |
|---|---|---|
| JP | 6070958 A | 3/1994 |
| JP | 2002542061 A | 12/2002 |
| JP | 2003033391 A | 2/2003 |
| WO | 8302442 A1 | 7/1983 |

OTHER PUBLICATIONS

Extended European Search Report issued Jul. 3, 2013 corresponds to EP Patent application No. 10812080.9.

Office Action mailed Jun. 11, 2013 corresponds to Japanese patent application No. 2009-200524.

* cited by examiner

FOLDING APPARATUS

RELATED APPLICATIONS

The application is a National Phase of International Application Number PCT/JP2010/064814, field Aug. 31, 2010, and claims priority from, Japanese Application Number 2009-200524, filed Aug. 31, 2009.

TECHNICAL FIELD

The present invention relates to a folding apparatus configured to fold a web conveyed in a machine direction which is in line with a flow direction of manufacturing processes of an absorbent article.

BACKGROUND ART

A method of manufacturing an absorbent article, such as a sanitary napkin and a diaper, includes a process of folding a sheet continuum or a web along a machine direction which is in line with a flow direction of manufacturing processes of the absorbent article, while conveying the sheet continuum or the web in the machine direction. For example, there is disclosed an apparatus which forms a gather by disposing a string-like elastic member on a web (see Patent Document 1).

Patent Document 1 discloses the following folding apparatus. Specifically, in the folding apparatus, a conveying path which a web travels becomes narrower in width from its upstream side toward its downstream side in a machine direction. The folding apparatus folds the web so that a side region of the web overlaps a central region of the web, the side region and the central region extending in the machine direction of the web. The web is folded by being controlled by guides for forming folds while being conveyed in the machine direction.

The technique disclosed in Patent Document 1, however, has the following problem. Specifically, at points of the web from which the web is folded (hereinafter the points are collectively called a "fold origin"), the web becomes narrower in width. Moreover, at the fold origin, the side regions of the web having been conveyed in a flat manner are folded toward the central region. Here, the conveying path on the downstream side of the fold origin is bent relative to the conveying path on the upstream side of the fold origin. For this reason, a large stress is applied on the web at the fold origin of the web.

The web is conveyed while being rubbed by proximal ends of the guides. When the conveying speed is increased, this rubbing causes more damage particularly at the fold origin of the web, thereby causing manufacturing failures such as tearing.

PRIOR ART DOCUMENT

Patent Document

[Patent Document 1] Japanese Patent Application Publication No. 2003-33391 (FIG. 2)

Summary of Invention

A folding apparatus (folding apparatus 100) according to a first aspect is configured to fold a web (web 200) conveyed in a machine direction (MD) which is in line with a flow direction of manufacturing processes of an absorbent article. The folding apparatus includes: a rotating body (pressing rolls 121, 122) including a rotational shaft orthogonal to the machine direction and configured to convey the web in the machine direction while pressing the web in a direction intersecting a surface of the web, and a guide unit (sailor plate 140, guides 141, 142) provided downstream of the rotating body in the machine direction, and configured to guide the web so that a side region (side regions 201, 202) of the web overlaps a central region (central region 203) of the web, the side region extending in the machine direction and the central region located on an inner side of the side region in a width direction of the web. At least one end of the rotating body has a tapered shape (tapered surfaces 121a, 122a) tapered toward a side edge portion of the web. The one end is disposed closer to a central region of the web than to the side edge portion.

DESCRIPTION OF EMBODIMENTS

A folding apparatus according to embodiments of the present invention will be described with reference to the drawings. Note that, in the following description of the drawings, same or similar reference signs denote same or similar elements and portions. In addition, it should be noted that the drawings are schematic and ratios of dimensions and the like are different from actual ones. Therefore, specific dimensions and the like should be determined in consideration of the following description. Moreover, the drawings also include portions having different dimensional relationships and ratios from each other.

Figure 1:
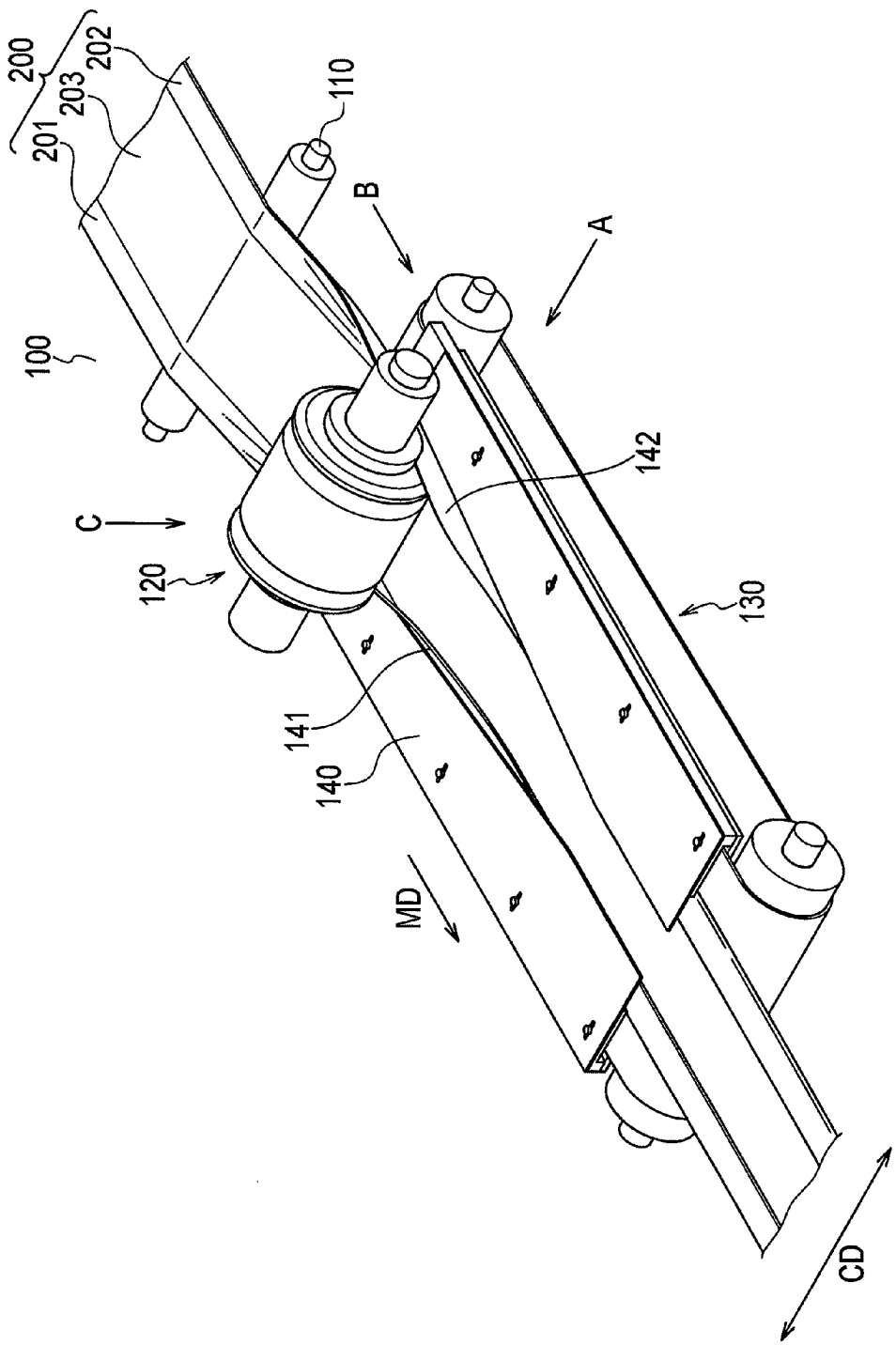
FIG. 1 is a perspective view illustrating a folding apparatus according to an embodiment of the present invention.
Figure 2:
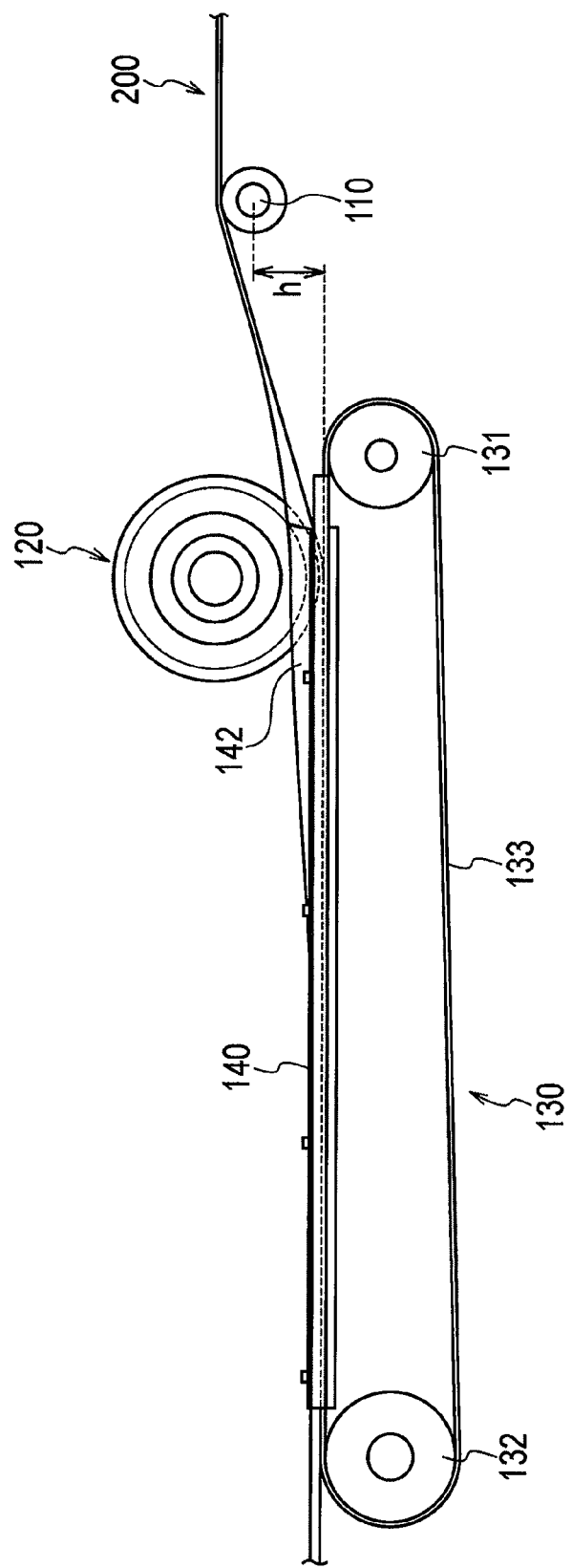
FIG. 2 is a side view of the folding apparatus when viewed in a direction of an arrow A shown in FIG. 1.
Figure 3:
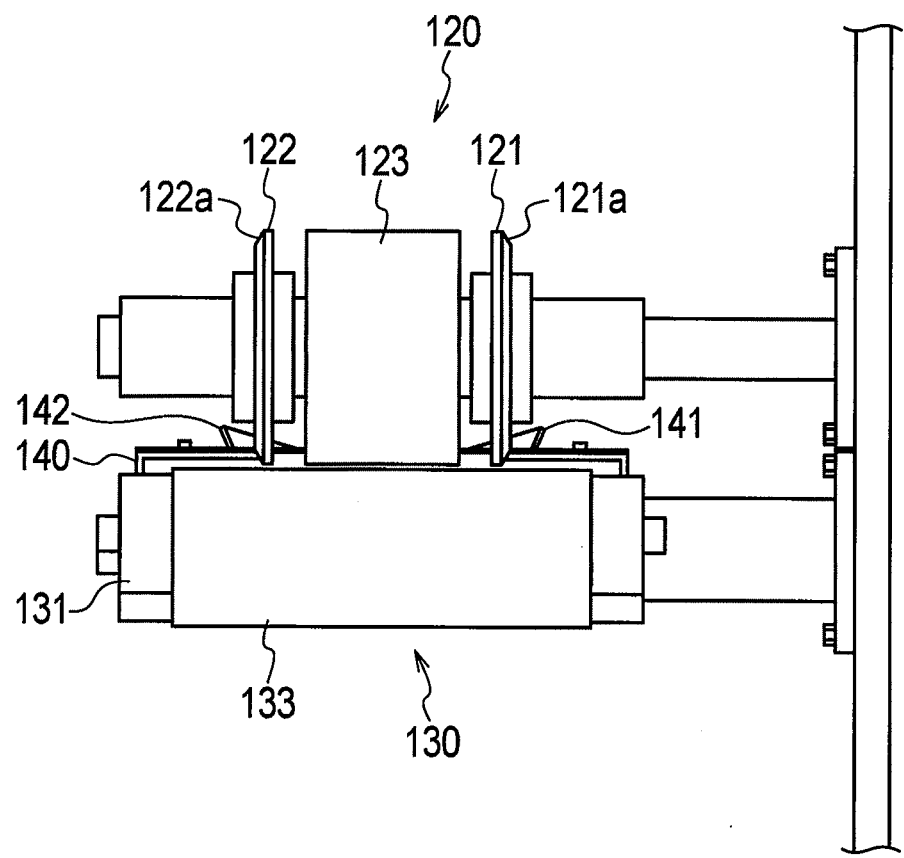
FIG. 3 is a front view of the folding apparatus when viewed in a direction of an arrow B shown in FIG. 1 (when viewed from the upstream side).

FIG. 1 is a perspective view illustrating a folding apparatus 100 according to an embodiment of the present invention. FIG. 2 is a side view of the folding apparatus when viewed in a direction of an arrow A shown in FIG. 1. FIG. 3 is a front view of the folding apparatus when viewed in a direction of an arrow B shown in FIG. 1.

The folding apparatus 100 includes a first roll 110, a sailor roll 120, a conveyor mechanism 130, and a sailor plate 140. The folding apparatus 100 is an apparatus configured to convey a continuum (web 200) in a machine direction MD while folding the web along a predetermined fold line, the machine direction MD being in line with the flow of manufacturing processes of an absorbent article or the like.

The first roll 110 is configured to convey the web 200 to the sailor roll 120 and the conveyor mechanism 130 which are located downstream of the first roll 110 in the machine direction MD. A rotational shaft of the first roll 110 is orthogonal to the machine direction MD. The length of the first roll 110 extending in a cross direction CD, which is orthogonal to the machine direction MD, is larger than the width of the web 200.

The sailor roll 120 is disposed downstream of the first roll 110 in the machine direction MD. A rotational shaft of the sailor roll 120 is orthogonal to the machine direction MD. Edge portions of the sailor roll 120 in the cross direction CD are disposed closer to a central region of the web 200 than to side regions 201, 202 (side edge portions) of the web 200. In other words, the length of the sailor roll 120 in the cross direction CD is smaller than the width of the web 200. The sailor roll 120 is disposed in a position which corresponds to a central region 203 of the web 200. The sailor roll 120 is configured to convey the web 200 in the machine direction MD while pressing at least the side regions 201, 202 of the web 200 in a direction intersecting a surface of the web 200. The sailor roll 120 will be described in detail later.

The conveyor mechanism 130 is disposed on a side of the web 200 opposite from the sailor roll 120. As shown in FIG. 2, the conveyor mechanism 130 includes a roller 131, a roller 132, and an endless belt 133 which is wound around the rollers 131, 132. The roller 131 or 132 rotates in the machine direction MD by a drive mechanism which is not illustrated. The conveyor mechanism 130 is equipped with a suction mechanism, and the endless belt 133 is provided with a suction port. With this configuration, the central region 203 of the web 200 is pressed against the endless belt 133 by the sailor roll 120 while being sucked onto a conveyance surface of the endless belt 133.

The sailor plate 140 includes a guide 141 and a guide 142. The sailor plate 140 is configured to guide the web 200 by use of the guides 141, 142 in such a way that the side regions 201, 202 of the web 200 conveyed in the machine direction MD are guided onto the central region 203. Specifically, the sailor plate 140 constitutes a guide portion.

In the folding apparatus 100, the first roll 110 is disposed at a position higher by a height h than the conveyance surface of the endless belt 133. In addition, the sailor roll 120 is smaller in width than the web 200, and is located at a position higher than the conveyance surface of the endless belt 133. This configuration causes a force to curl the side regions 201, 202 of the web 200, which are not pressed by the sailor roll 120, up toward the sailor roll 120 from the conveyance surface of the endless belt 133. The curled side regions 201, 202 are guided by the guides 141, 142 so as to be tilted toward the central region 203, and thus the web 200 is folded.

Subsequently, the sailor roll 120 is described in detail. FIG. 3 is a front view of the folding apparatus when viewed in a direction of an arrow B shown in FIG. 1. For simplifying the explanation, FIG. 3 does not illustrate the web 200. The sailor roll 120 includes a pair of pressing rolls 121, 122 and a center roll 123. The pressing rolls 121, 122 are configured to press down the web 200 while the center roll 123 is disposed between the pressing rolls 121, 122 and is configured to press down the central region 203 of the web 200. The portions of the web 200 pressed down by the pressing rolls 121, 122 serve as a fold origin from which the web 200 is folded. The pressing rolls 121, 122 each constitute a rotating body. The center roll 123 constitutes a sub rotating body.

The pressing rolls 121, 122 are movable to any position as long as the position is located on an inner side of the side regions 201, 202 of the web 200 and on an outer side of the center line CL extending along the machine direction MD. Moreover, the pressing rolls 121, 122 are attachable to and detachable from a shaft core.

Each of the pressing rolls 121, 122 has a tapered shape in which the diameter becomes smaller toward the outer side in the cross direction CD. The pressing rolls 121, 122 have tapered surfaces 121a, 122a, respectively. It is preferable that the surfaces of the pressing rolls 121, 122 be subjected to surface processing. For example, matt finishing is applied to at least surfaces of the pressing rolls 121, 122 which come into contact with the web 200. This matt finishing causes embossed portions to be formed on the surfaces.

Fiber of 1 to 2 decitex (dtex) is used for a web of a general absorbent article. Applying of the matt finishing to at least the surfaces of the pressing rolls 121, 122 which come into contact with the web 200 has the following advantage. Specifically, each of the raised portions formed on the surfaces of the pressing rolls 121, 122 enters a gap between fibers and picks up the fibers, thereby increasing the sliding frictional resistance.

In addition, the at least surfaces of the pressing rolls 121, 122 which come into contact with the web 200 are processed to be nonadhesive. It is particularly preferable that the at least surfaces of the pressing rolls 121, 122 which come into contact with the web 200 be subjected to plasma coating. The surfaces can be satin-processed also by the plasma coating.

Figure 4:
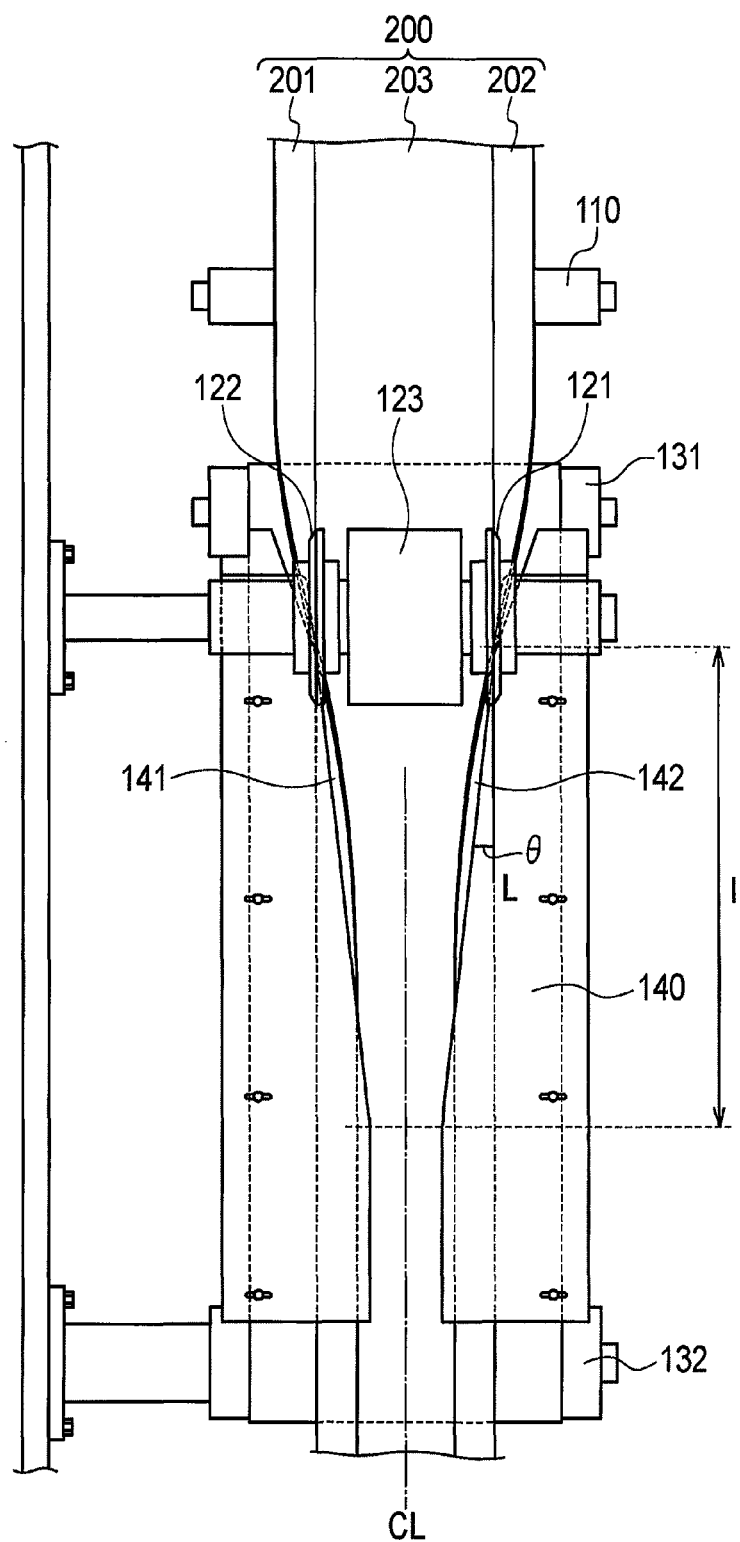
FIG. 4 is a plan view of the folding apparatus when viewed in a direction of an arrow C shown in FIG. 1 (when viewed from the top).

FIG. 4 is a plan view of the folding apparatus 100 when viewed in a direction of an arrow C shown in FIG. 1. Each of the guides 141, 142 is disposed downstream of a contact point where a corresponding one of the pressing rolls 121, 122 come into contact with the web 200. Each of the guides 141, 142 is disposed so as to intersect an imaginary line L at an angle θ, the imaginary line L being drawn from the contact point toward the downstream side of the contact point in the machine direction MD.

As having the tapered surfaces 121a, 122a, the pressing rolls 121, 122 allow each of the guides 141, 142 formed in the sailor plate 140 to intersect the imaginary line L at an angle θ. Accordingly, a gap between the guides 141, 142 formed in the sailor plate 140 can be made small. Thus, when a part of the web 200 is to be folded with a defined fold margin, the guides 141, 142 formed in the sailor plate 140 can hold the web 200 at a region closer to a fold line of the web 200. In other words, with this configuration, portions of the web 200 can be overlapped with one another with a higher accuracy.

In addition, the pressing rolls 121, 122 rotate while conveying the web 200. Therefore, the relative velocity between the web 200 and each of the pressing rolls 121, 122 is zero at the fold origin where the pressing rolls 121, 122 come into contact with the web 200. Since the web 200 and each of the pressing rolls 121, 122 do not rub each other as described above, less damage is caused on the web 200 during the folding process. Furthermore, the tapered surfaces 121a, 122a of the pressing rolls 121, 122 form an angle larger than 90° (an obtuse angle) in a cross section when viewed in the flow direction of the folding apparatus 100. Hence, less damage is caused on the web 200.

As has been described above, during the folding of the web 200, the folding apparatus 100 is capable of reducing damage to be caused on the web 200, and of folding the web 200 neatly along the fold line.

According to the folding apparatus 100, the surfaces of the pressing rolls 121, 122 are subjected to surface processing to be nonadhesive. With this processing, even if the web 200 has an adhesive, such as a hot-melt, applied on its surface, the web 200 can be folded without being erroneously wound around the pressing rolls 121, 122. The folding apparatus 100 is also applicable to, for example, a process of folding back a part of a web after a string-like elastic member is disposed on the web (a process of manufacturing a so-called gather).

In the folding apparatus 100, the surfaces of the pressing rolls 121, 122 are subjected to matt finishing. This matt finishing increases the sliding frictional resistance against the web 200, and thus enhances so-called grip or traction. Accordingly, the side regions 201, 202 of the web 200 are more likely to be picked up by the surfaces of the pressing rolls 121, 122 on the downstream side thereof, and thus are more easily curled toward the sailor roll 120. For this reason, the folding apparatus 100 is capable of preventing a phenomenon in which the width of the web 200 is reduced in the width direction at or around the fold portions which are pressed by the pressing rolls 121, 122, and of conveying the side regions 201, 202 of the web 200 along the guides 141, 142. Accordingly, the folding apparatus 100 is capable of forming the fold portions in a stable manner.

The folding apparatus 100 includes the center roll 123 which is disposed between the pressing rolls 121, 122 and configured to press the central region 203 of the web 200. Using the surface processing of the pressing rolls 121, 122 in combination with the center roll 123 allows stable pressing and holding of the entire central region 203. This helps the side regions 201, 202 to be curled outward in an accurate manner by the pressing rolls 121, 122. Moreover, the central region 203 of the web 200 is also held by the center roll 123. This can prevent a phenomenon in which the web 200 is curled in an unbalanced manner, being one-sided on either one of the pressing rolls 121, 122 and thus the center line CL of the web 200 in the width direction is misaligned with the center of the pressing rolls 121, 122 in the width direction. Accordingly, the fold portions are formed in a stable manner.

In addition, the folding apparatus 100 can cope with size change or change in the fold margin of the web 200, since the pressing rolls 121, 122 are made movable toward outer sides of the center line CL of the web 200. Furthermore, since the pressing rolls 121, 122 are made attachable to and detachable from the shaft core, the pressing rolls 121, 122 can be replaced with new ones when worn out. This enhances the workability including ease of maintenance of the folding apparatus 100.

The folding apparatus 100 of the present embodiment is applicable to a folding process of a continuum of top sheets, back sheets, or other components of an absorbent article. The material of the web 200 foldable by the folding apparatus 100 is not particularly limited as far as the web 200 is in a sheet form and is made of a non-woven fabric, a woven fabric, a perforated plastic sheet, or the like. The raw material of the non-woven fabric or the woven fabric may be any of natural fibers and chemical fibers.

Examples of the natural fibers include ground pulp and cellulose such as cotton. Examples of the chemical fibers include regenerated cellulose such as rayon and fibrillated rayon, semi-synthetic cellulose such as acetate and triacetate, thermoplastic hydrophobic chemical fibers, and thermoplastic hydrophobic chemical fibers subjected to a hydrophilic treatment. Examples of the thermoplastic hydrophobic chemical fibers include single fibers such as polyethylene (PE), polypropylene (PP), or polyethylene terephthalate (PET), fibers obtained through graft polymerization of polyethylene and polypropylene, and compound fibers having a core-in-sheath structure.

The web 200 may be a nonwoven fabric sheet, a spunlace, or the like. The nonwoven fabric sheet is formed by a web forming method such as a dry method (a carding method, a spunbond method, a melt-blown method, an air-laying method or the like) or a wet method. The spunlace is formed into a sheet by hydroentanglement. Furthermore, the web 200 may be a nonwoven fabric having projections and depressions on its upper layer side or a nonwoven fabric having projections and depressions so as to have variations in mass per unit area by being applied air during web forming.

In addition, as a moisture impermeable sheet, a film mainly formed of polyethylene, polypropylene, or the like, a breathable resin film, a sheet obtained by bonding a breathable resin film onto a nonwoven fabric such as a spunbond, a spunlace, or the like can be used.

Other Embodiments

As described above, the details of the present invention have been disclosed by using the embodiment of the present invention. However, it should not be understood that the description and drawings which constitute part of this disclosure limit the present invention. From this disclosure, various alternative embodiments, examples, and operation techniques will be easily found by those skilled in the art.

Although not illustrated in the present embodiment, a different roll may be provided on a side of the web 200 opposite from the first roll 110, the different roll configured to hold the web 200 together with the first roll 110 by sandwiching the web 200. Provision of the different roll has the following advantage. Specifically, the side regions 201, 202 of the web 200 which are curled by the sailor roll 120 stop curling at the position of the first roll 110. This can prevent a problem which would otherwise occur if the side regions 201, 202 should curl further toward the upstream side.

In the present embodiment, the description is given that a pair of the press rolls 121, 122 are provided on the right and left sides in the width direction. However, the press rolls are not limited to the pair of the press rolls 121, 122. For example, a single press roll may be provided depending on a fold position of the web.

Moreover, although the center roll 123 has a function of pressing the central region 203 of the web 200 to enhance the curling of the side regions 201, 202, the folding apparatus 100 does not have to include the center roll 123.

As described above, the present invention naturally includes various embodiments which are not described herein. Accordingly, the technical scope of the present invention should be determined only by the matters to define the invention in the scope of claims regarded as appropriate based on the description.

Note that, the entire content of Japanese Patent Application No. 2009-200524 (filed on Aug. 31, 2009) is incorporated herein by reference.

INDUSTRIAL APPLICABILITY

The present invention is able to provide a folding apparatus which is capable of folding a web neatly along a fold line while causing less damage on the web in a folding process of the web.

The invention claimed is:

1. A folding apparatus configured to fold a web conveyed in a machine direction which is in line with a flow direction of manufacturing processes of an absorbent article, the folding apparatus comprising:
   a rotating body including a rotational shaft orthogonal to the machine direction and configured to convey the web in the machine direction while pressing the web in a direction intersecting a surface of the web, and
   a guide unit provided downstream of the rotating body in the machine direction, and configured to guide the web so that a side region of the web overlaps a central region of the web, the side region extending in the machine direction and the central region located on an inner side of the side region in a width direction of the web,
   wherein the rotating body presses down a fold origin of the web and
   wherein
   at least one end of the rotating body is tapered toward a side edge portion of the web, and the one end is disposed closer to the central region of the web than to the side edge portion, and
   a raised portion is formed on at least one surface of the rotating body, the surface coming into contact with the web, the raised portion entering a gap between fibers forming the web.

2. The folding apparatus according to claim 1, wherein the at least one surface of the rotating body which is configured to come into contact with the web is nonadhesive.

3. The folding apparatus according to claim 1, further comprising a sub rotating body,
wherein
the rotating body comprises first and second rotating bodies, and the sub rotating body is provided between the first and second rotating bodies, and
the sub rotating body configured to press the central region of the web which is located on an inner side of the side edge portion in the width direction.

4. The folding apparatus according to claim 1, wherein the rotating body is movable to any position inward of the side edge portion of the web and outward of a center line in the width direction, the center line extending in the machine direction.

5. The folding apparatus according to claim 1, further comprising a sub rotating body,
wherein the rotating body comprises a pair of first and second rotating bodies provided respectively on both sides of the sub rotating body in the width direction.

* * * * *